US009039682B2

(12) United States Patent
Lampropoulos et al.

(10) Patent No.: US 9,039,682 B2
(45) Date of Patent: May 26, 2015

(54) SUTURE SECUREMENT APPARATUS

(75) Inventors: Fred P. Lampropoulos, Salt Lake City, UT (US); Timothy W. Clark, Philadelphia, PA (US); Gregory R. McArthur, Sandy, UT (US); Michael Joseph Ferlic, Roseville, MN (US)

(73) Assignee: Merit Medical Systems, Inc., South Jordan, UT (US)

(*) Notice: Subject to any disclaimer, the term of this patent is extended or adjusted under 35 U.S.C. 154(b) by 1173 days.

(21) Appl. No.: 12/404,227

(22) Filed: Mar. 13, 2009

(65) Prior Publication Data
US 2009/0234295 A1  Sep. 17, 2009

Related U.S. Application Data

(60) Provisional application No. 61/036,916, filed on Mar. 14, 2008.

(51) Int. Cl.
*A61M 25/02* (2006.01)
*A61B 17/04* (2006.01)
(Continued)

(52) U.S. Cl.
CPC ....... *A61M 25/02* (2013.01); *A61M 2025/0266* (2013.01); *A61M 2025/0273* (2013.01);
(Continued)

(58) Field of Classification Search
CPC .............. A61M 25/02; A61B 17/0482; A61B 17/0483; A61B 17/0485; A61B 17/0487; A61B 17/0401; A61B 17/0469; A61B 19/0256
USPC ............ 606/139, 148, 232; 24/115 R, 116 R, 24/116 A, 130, 136 R, 115 F, 115 G, 291, 24/292
See application file for complete search history.

(56) References Cited

U.S. PATENT DOCUMENTS 3,215,027 A * 11/1965 Modrey et al. ................. 411/76
3,452,740 A    7/1969 Muller
(Continued)

FOREIGN PATENT DOCUMENTS

EP        534747       3/1993
WO    WO 01/41860     6/2001

OTHER PUBLICATIONS

Notification of Transmittal of the International Searching Report and the Written Opinion of the International Searching Authority issued Dec. 14, 2007 in International Application No. PCT/US2007/06945.
(Continued)

*Primary Examiner* — Dianne Dornbusch
(74) *Attorney, Agent, or Firm* — Stoel Rives LLP (57) ABSTRACT

A suture securement apparatus for selectively securing one or more ends of a suture while allowing adjustments in the tension or a full release of the sutures intermittently after a prolonged period of time. The suture securement apparatus can be particularly adapted for use with a purse-string suture to close a percutaneous catheter insertion site without causing puckering or distortion of the skin at the purse string suture site. The suture securement apparatus allows for subsequent modification of the amount of tensioning or full release of the sutures at the catheter insertion site. A threading assembly for use with the suture securement apparatus and being adapted to facilitate threading of sutures along the length of the suture securement apparatus. An adhesive suture securement device to provide securing sutures to be utilized with a suture securement apparatus. An adhesive securement device to provide a cradle configured to secure a hub of a catheter or other medical instrument or device.

21 Claims, 7 Drawing Sheets

(51) Int. Cl.
*A61B 19/02* (2006.01)
*A61B 19/08* (2006.01)
*A61B 17/00* (2006.01)

(52) U.S. Cl.
CPC .. *A61M2025/028* (2013.01); *A61M 2025/0286* (2013.01); *A61B 17/0482* (2013.01); *A61B 17/0483* (2013.01); *A61B 17/0485* (2013.01); *A61B 17/0487* (2013.01); *A61B 19/0256* (2013.01); *A61B 2019/085* (2013.01); *A61B 2017/00637* (2013.01); *A61B 2017/00663* (2013.01)

(56) References Cited

U.S. PATENT DOCUMENTS

| | | | |
|---|---|---|---|
| 4,102,478 | A | 7/1978 | Samoilov |
| 4,796,626 | A | 1/1989 | DeVries |
| 4,799,496 | A | 1/1989 | Hargreaves et al. |
| 4,829,999 | A | 5/1989 | Auth |
| 4,858,810 | A | 8/1989 | Intlekofer et al. |
| 4,860,742 | A | 8/1989 | Park et al. |
| 4,957,117 | A | 9/1990 | Wyaham |
| 4,973,329 | A | 11/1990 | Park et al. |
| 5,137,517 | A | 8/1992 | Loney et al. |
| 5,161,534 | A | 11/1992 | Berthiaume |
| 5,219,332 | A | 6/1993 | Nelson et al. |
| 5,312,338 | A | 5/1994 | Nelson et al. |
| 5,325,746 | A | 7/1994 | Anderson |
| 5,325,868 | A | 7/1994 | Kimmelstiel |
| 5,392,778 | A | 2/1995 | Horzewski |
| 5,423,331 | A | 6/1995 | Wysham |
| 5,634,475 | A | 6/1997 | Wolvek |
| 5,741,301 | A | 4/1998 | Pagedas |
| 5,800,447 | A * | 9/1998 | Wenstrom, Jr. ............... 606/139 |
| 5,851,189 | A | 12/1998 | Forber |
| 5,919,161 | A | 7/1999 | Hill, III et al. |
| 5,987,344 | A | 11/1999 | West |
| 6,015,428 | A | 1/2000 | Pagedas |
| 6,030,349 | A | 2/2000 | Wilson et al. |
| 6,033,414 | A | 3/2000 | Tockman et al. |
| 6,059,484 | A | 5/2000 | Greive |
| 6,171,317 | B1 | 1/2001 | Jackson et al. |
| 6,371,940 | B1 | 4/2002 | Valencia et al. |
| 6,394,976 | B1 | 5/2002 | Winston et al. |
| 6,533,772 | B1 | 3/2003 | Sherts et al. |
| 6,626,917 | B1 | 9/2003 | Craig |
| 6,949,104 | B2 | 9/2005 | Griffis et al. |
| 7,011,635 | B1 | 3/2006 | Delay |
| 7,087,060 | B2 * | 8/2006 | Clark ............................. 606/111 |
| 7,144,378 | B2 | 12/2006 | Arnott |
| 7,416,556 | B2 * | 8/2008 | Jackson ......................... 606/232 |
| 7,785,348 | B2 * | 8/2010 | Kuhns et al. .................. 606/232 |
| 7,850,712 | B2 * | 12/2010 | Conlon et al. ................. 606/232 |
| 7,866,909 | B2 * | 1/2011 | Denmark ...................... 403/353 |
| 7,947,053 | B2 * | 5/2011 | McKay et al. ................. 606/148 |
| 7,972,282 | B2 * | 7/2011 | Clark et al. .................... 600/585 |
| 8,105,355 | B2 | 1/2012 | Page et al. |
| 2001/0031973 | A1 | 10/2001 | Nobles et al. |
| 2003/0028203 | A1 | 2/2003 | Clark |
| 2003/0158581 | A1 * | 8/2003 | Levinson ....................... 606/232 |
| 2003/0225395 | A1 | 12/2003 | Griffis et al. |
| 2003/0229297 | A1 | 12/2003 | Christensen et al. |
| 2004/0067099 | A1 | 4/2004 | Warburton-Pitt |
| 2004/0215108 | A1 | 10/2004 | Windheuser |
| 2005/0070820 | A1 | 3/2005 | Boutillette et al. |
| 2005/0096566 | A1 | 5/2005 | Arnott |
| 2005/0235778 | A1 | 10/2005 | Murphy et al. |
| 2006/0030886 | A1 * | 2/2006 | Clark ............................. 606/232 |
| 2007/0106308 | A1 | 5/2007 | Onuki et al. |
| 2007/0112385 | A1 * | 5/2007 | Conlon ......................... 606/232 |
| 2007/0142786 | A1 | 6/2007 | Lampropoulos et al. |
| 2007/0219467 | A1 * | 9/2007 | Clark et al. .................... 600/585 |
| 2008/0269785 | A1 | 10/2008 | Lampropoulos et al. |
| 2010/0057110 | A1 | 3/2010 | Lampropoulos et al. |

OTHER PUBLICATIONS

Notification of Transmittal of the International Search Report and the Written Opinion of the International Searching Authority issued Jun. 25, 2009 in International Application No. PCT/US2009/037168.
European Search Report issued May 29, 2009 in co-pending European patent application No. 07753564.9.
Vorwerk, Konner, Schurmann, and Gunther, a Simple Trick to Facilitate Bleeding Control after Percutaneous Hemodialysis Fistula and Graft Interventions, Cardiovasc Intervent Radiol 20 (2) : 159-60 (1997).
Zaleski, Funaki, Gentile, and Garofalo, Purse-string Sutures and Miniature Tourniquet to Achieve Immediate Hemostasis of Percutaneous Grafts and Fistulas: a Simple Trick with a Twist, Am. J. Roentgenol. 175 (6) : 1643-5 (2000).
Simmons, Clark, and Rajan, The Woggle Technique: A New Method of Suture Closure of Hemodialysis Arteriovenous Grafts and Fistulae After Percutaneous Intervention, Journal of Vascular and Interventional Radiology 12(1) :S30 (2001).
Notice of Allowance issued Jan. 10, 2006 in co-pending U.S. Appl. No. 10/198,161.
Response and Amendment filed Oct. 6, 2005 in co-pending U.S. Appl. No. 10/198,161.
Office Action issued Apr. 6, 2005 in co-pending U.S. Appl. No. 10/198,161.
Office Action issued Feb. 7, 2005 in co-pending U.S. Appl. No. 10/198,161.
Preliminary Amendment filed Oct. 6, 2005 in co-pending U.S. Appl. No. 11/244,168.
Office Action issued Feb. 6, 2007 in co-pending U.S. Appl. No. 11/244,168.
Amendment filed Aug. 6, 2007 in co-pending U.S. Appl. No. 11/244,168.
Examiner Interview Summary in co-pending U.S. Appl. No. 11/244,168.
Office Action issued Oct. 18, 2007 in co-pending U.S. Appl. No. 11/244,168.
Notice of Abandonment issued Aug. 7, 2008 in co-pending U.S. Appl. No. 11/244,168.
Office action dated Jun. 11, 2010 in U.S. Appl. No. 11/688,766.
Office action dated Mar. 16, 2010 in U.S. Appl. No. 11/688,766.
Office action dated Oct. 24, 2011 in U.S. Appl. No. 12/202,073.
Restriction Requirement dated Feb. 2, 2011 for U.S. Appl. No. 12/202,073.
Office Action dated May 4, 2011 for U.S. Appl. No. 12/202,073.
Restriction Requirement dated Mar. 16, 2010 for U.S. Appl. No. 11/688,766.
Office Action dated Jun. 11, 2010 for U.S. Appl. No. 11/688,766.
Notice of Allowance dated Apr. 28, 2011 for U.S. Appl. No. 11/688,766.
Office Action dated Dec. 10, 2013 for U.S. Appl. No. 12/202,073.
Office Action dated May 27, 2014 for U.S. Appl. No. 12/202,073.

* cited by examiner

SUTURE SECUREMENT APPARATUS

CROSS REFERENCE TO RELATED APPLICATIONS

This application claims the benefit of U.S. Provisional Patent Application No. 61/036,916, filed on Mar. 14, 2008, the entire contents of which are herein incorporated by reference.

BACKGROUND OF THE INVENTION

1. Field of the Invention

The present invention relates to a suture securement apparatus. In more particular, the present invention relates to a suture securement apparatus and adhesive suture securement devices which can be utilized in connection with a threading assembly to provide desired securement of a introducer sheath apparatus and/or closure of a percutaneous catheter insertion site.

2. Relevant Technology

Some of the challenges encountered with a percutaneous catheter insertion relate to the maintaining of the catheter within the catheter insertion site and also the proper maintenance of hemostasis subsequent to removal of the catheter from the catheter insertion site. A variety of different suturing techniques have been utilized in connection with the puncture wound of percutaneous catheter insertion sites and the maintenance of catheters within the percutaneous catheter insertion sites. However, inadvertent slipping or removal of catheters and desired closure of puncture wounds of percutaneous catheter insertion sites subsequent to removal of such catheters has resulted in undesirable patient discomfort and potentially a loss of hemostasis.

One of the techniques often utilized with percutaneous catheter insertion sites is the use of a purse string suture. A purse string suture is formed by inserting a suture, such as a monofilament or braided thread into the patient's skin at a position adjacent the insertion site. The practitioner then forms a circular series of continuous stitches which parallel the edges of the wound in a substantially circular pattern. The configuration of the stitches results in a plurality of segments of suture which alternate between being threaded under a portion of the patient's skin and being positioned over the surface of the patient's skin such that the stitch has between three and four segments or stitches which are positioned above the skin around the edges of the insertion site. A tail of the suture is left both at the initial insertion site of the suture and also at the emergent site of the suture such that the purse string suture appears to have two tails which emerge somewhat close in proximity to one another at a predetermined point around the edges of the insertion site.

The purse string sutures allow a practitioner to close the puncture wound of the insertion site by simply pulling on the two ends of the suture, thus tightening the suture which is then threaded around the perimeter of the insertion site effectively closing the puncture wound of the insertion site and providing the desired hemostasis. In this manner, excessive compression and other techniques which are typically utilized to stop puncture wound bleeding are not needed.

One of the challenges which has been experienced with purse string suture closure methods and the desired maintenance of hemostasis utilizing the purse string suture relates to the knotting or other techniques for maintaining tension on the adjacent ends of the purse string suture. One mechanism which has been utilized employs a knot at one end of one suture which engages the other suture to maintain the desired tension of the overall length of the purse string suture. However, the knot utilized in connection with such techniques can compromise the integrity of the purse string suture. Additionally, the knot can make subsequent loosening and retightening of the purse string suture difficult if not impractical. Additionally, non-doctor practitioners may be unwilling or uncomfortable with removing such sutures at the end of the procedure. As a result, the doctor must see the patient to remove the suture, or the patient may be required to come in for an office visit that may be inconvenient or otherwise unnecessary.

Another technique which has been utilized is to attempt to utilize a secondary securement apparatus to secure the ends of the suture. However, such techniques utilizing existing secondary securement apparatus often result in excessive tension on the purse string suture which can cause puckering or unnatural distortion of the patient's skin adjacent the purse string suture site. As a result, unnecessary discomfort and/or damage to the patient tissue can result. Moreover, existing secondary securement apparatus can compromise the integrity of the suture, giving rise to the potential that the suture will break. If the suture breaks, there is a risk that hemostasis at the insertion site will be lost and/or slipping of the catheter will occur resulting in partial or total removal of the catheter from the insertion site.

BRIEF SUMMARY OF THE INVENTION

The present disclosure relates to a suture securement apparatus and adhesive suture securement devices which can be utilized to provide desired securement of a introducer sheath apparatus and/or closure of a percutaneous catheter insertion site. A suture securement apparatus can be configured to selectively secure one or more ends of a suture while allowing adjustments in the tension or a full release of the suture in a quick, simple and effective manner. The suture securement apparatus can be utilized in connection with a purse string suture at a percutaneous catheter insertion site to achieve desired hemostasis. A threading assembly can be utilized to quickly and simply thread one or more tails of the purse string suture through a lumen of the suture securement apparatus to enable engagement of the tails of the suture. The extension tube of the suture securement apparatus can be configured to facilitate drawing the tails of the purse string suture together to achieve and maintain a desired degree of tension to close the insertion site and achieve hemostasis. Moreover, pressing the release button of the suture securement apparatus can release the suture to permit a practitioner to subsequently modify the amount of tension, to alter the position of the suture securement apparatus relative to the patient, or to fully release the suture.

The present disclosure also relates to a threading assembly which can be utilized in connection with a suture securement apparatus to thread a suture through a lumen of the suture securement apparatus. The threading assembly comprises a clasp and a wire. The wire has one or more pre-formed bends to form an insertion assembly having a pointed tip and one or more angular portions defining an opening through which sutures can easily be inserted. The threading assembly is inserted through the lumen of the suture securement apparatus such that the opening of the insertion assembly is positioned distal to the suture securement apparatus. The ends of a suture can be inserted through the opening, such that as the threading assembly is drawn through the lumen of the suture securement apparatus the ends of the suture are also drawn through the lumen of the suture securement apparatus.

The present disclosure also relates to an adhesive suture securement device for providing securing sutures which can be utilized during a procedure without requiring insertion of the sutures through the patient's skin. The adhesive suture securement device has an adhesive base and one or more sutures secured to the adhesive base by an anchor. A practitioner can secure the adhesive base to the skin of a patient and the one or more sutures can then be utilized, for example, to secure a suture ring of a catheter hub relative to the patient. A suture securement apparatus and threading assembly can be utilized to thread the sutures through the ring of the catheter hub and thereby secure the catheter hub relative to the patient.

The present disclosure also relates to an adhesive securement device having a cradle in which a hub of a catheter can be secured. The adhesive securement device has an adhesive pad and a cradle configured to receive a hub of a catheter. The cradle can be secured to the adhesive base by a cradle base. The cradle can be configured such that the hub can snap into the cradle, thereby securing the hub relative to the skin of the patient.

DETAILED DESCRIPTION

Some of the challenges encountered with percutaneous catheter insertion relate to the maintaining of the catheter within the catheter insertion site and also the proper maintenance of hemostasis subsequent to removal of the catheter from the catheter insertion site. In some cases, a drainage catheter or other catheter or introducer sheath is left in place for a period of time, remaining inserted for use during subsequent procedures. When the drainage catheter remains inserted for extended periods, it can be important to secure the end of the catheter relative to the skin of the patient to guard against inadvertent movement of the catheter or removal of the catheter from the insertion site. Moreover, achieving hemostasis at the insertion site while the catheter is inserted and after the catheter is removed guards against blood loss and transfer of disease both to and from the patient.

A variety of different suturing techniques have been utilized in connection with percutaneous catheter insertion sites and the maintenance of catheters within the percutaneous catheter insertion sites. However, inadvertent slipping or removal of catheters and closure of percutaneous catheter insertion sites subsequent to removal of such catheters has resulted in undesirable patient discomfort and potentially a loss of hemostasis. As an example, practitioners commonly utilize a purse string suture at an insertion site as a technique to secure a introducer sheath and/or maintain hemostasis at the insertion site both while the catheter is inserted and after the catheter is removed. As described above, a purse string suture allows a practitioner to close the insertion site by simply pulling on the two ends or tails of the suture, thus tightening the suture. However, a challenge experienced when utilizing a purse string suture is maintaining tension on the ends of the purse string suture. Knotting the ends of the suture is problematic because the purse string cannot be easily loosened and subsequently retightened. Use of an existing secondary securement apparatus to secure the ends of the suture often results in excessive tension on the purse string suture, which can cause puckering or unnatural distortion of the patient's skin adjacent the purse string suture site. Moreover, existing secondary securement apparatus can be awkward to manipulate and can compromise the integrity of the suture.

An additional challenge of using a purse string suture is encountered when the condition of the patient's skin is poor (e.g., due to injury, disease, neglect, etc.). In these situations, the patient's skin near the insertion site may be thin or of such poor quality that the skin cannot accommodate the purse string suture and tears as a result of tension on the suture when the suture is tightened. Merely securing a introducer sheath, to guard against inadvertent slipping and prevent additional damage to the skin, becomes a significant challenge.

The present disclosure relates to a suture securement apparatus and adhesive suture securement devices that address these challenges. A suture securement apparatus and adhesive suture securement devices are provided which can be utilized in connection with a threading assembly to provide desired securement of a introducer sheath apparatus and/or maintain hemostasis at a percutaneous catheter insertion site.

Figures 1, 1A:
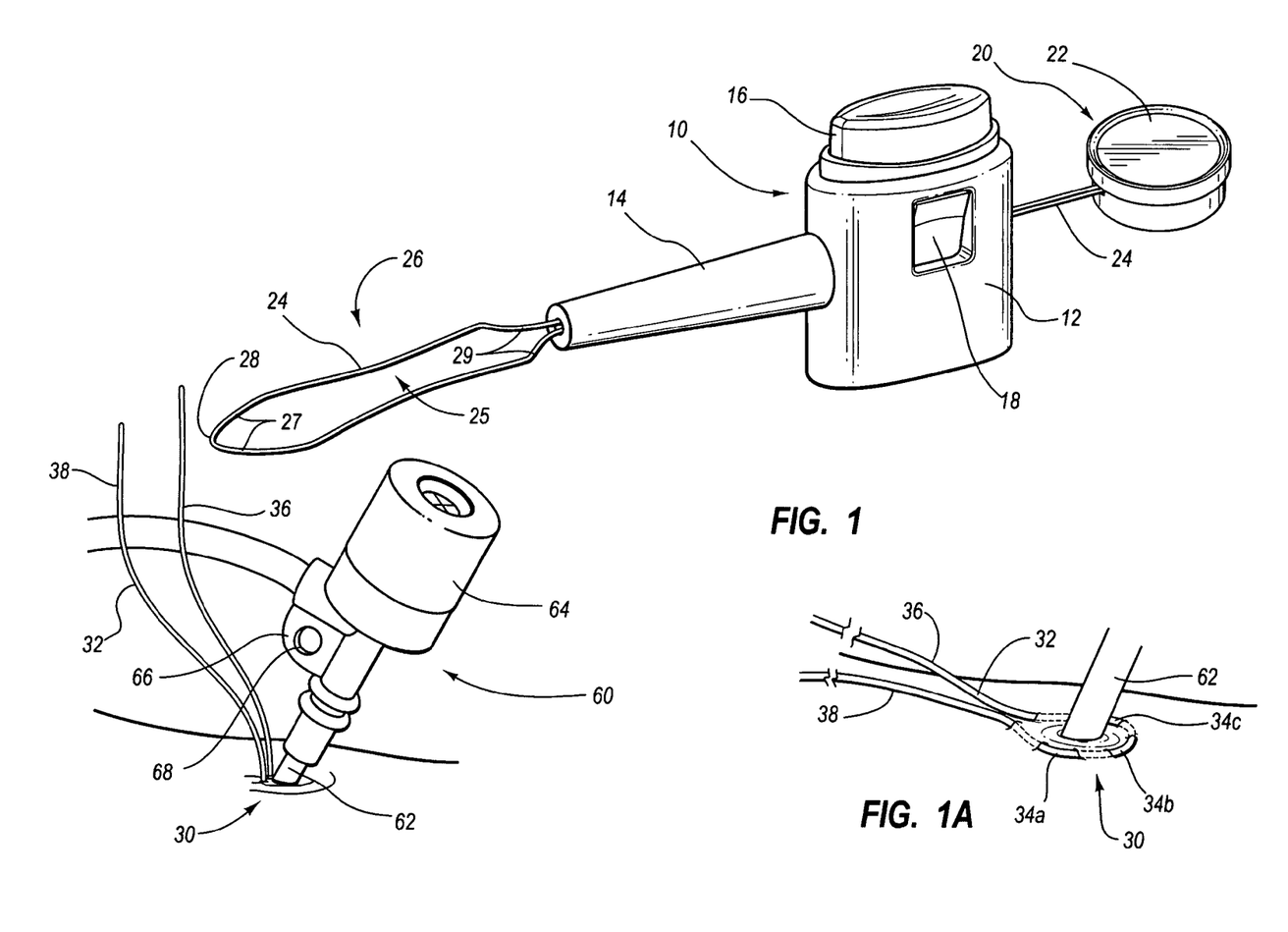
FIGS. 1 and 1A illustrate a suture securement apparatus having a threading assembly adapted for use with a suture ring of a catheter hub according to one embodiment of the present invention.

FIG. 1 is a perspective view of a suture securement apparatus according to one embodiment of the present invention. In the illustrated embodiment, suture securement apparatus 10 can be utilized to selectively and releasably secure the ends or tails 36, 38 of a suture utilized in various securement procedures. The suture is configured in a purse string suture configuration (as best depicted in FIG. 1A) to maintain hemostasis and close a percutaneous catheter insertion site 30. In the illustrated embodiment, suture securement apparatus 10 comprises a body 12, an extension tube 14, a release button 16, and an assembly window 18. Body 12 comprises a housing for securing the other components of suture securement apparatus 10 to maintain desired operability of the components of suture securement apparatus 10. An extension tube 14 extends distally from body 12. Extension tube 14 provides a mechanism for engaging suture 32 positioned adjacent insertion site 30 without interruption or interference from body 12 of suture securement apparatus 10.

Release button 16 is positioned within a cavity of body 12 of suture securement apparatus 10. Release button 16 allows a practitioner to selectively secure or release sutures positioned within suture securement apparatus 10. For example, in the illustrated embodiment when release button 16 is in a released position, suture securement apparatus 10 is securely gripping any sutures positioned within suture securement apparatus 10. When the user depresses release button 16, the grip exerted by suture securement apparatus 10 on any sutures positioned within suture securement apparatus 10 is loosened, and manipulation or adjustment of the suture securement apparatus 10 relative to the sutures can be effectuated. The ability to selectively release and reposition the suture securement apparatus 10 relative to sutures for which the suture securement apparatus 10 is to be utilized can be desirable to the extent the practitioner desires to adjust the tension, reposition suture securement apparatus 10 relative to the patient, or perform other desired activities relative to the sutures and/or suture securement apparatus 10. Assembly window 18 allows for the quick snap fit assembly of the release button 16 relative to body 12 of suture securement apparatus 10.

As illustrated in FIG. 1, suture securement apparatus 10 is utilized with a threading assembly 20. Threading assembly 20 allows a practitioner to quickly and simply thread one or more tails 36, 38 of suture 32 from the exterior of suture securement apparatus 10, through a lumen of suture securement apparatus 10 such that desired engagement of tails 36, 38 of suture 32 is effectuated. In the illustrated embodiment, threading assembly 20 comprises a clasp 22 and a wire 24. Clasp 22 is utilized to retain wire 24 in its desired position to prevent inadvertent advancement of the end of the wire 24 into suture securement apparatus 10.

Wire 24 is configured to form an insertion assembly 26. Insertion assembly 26 can comprise a pointed tip 28, an opening 25, and/or one or more angular portions 27 to allow insertion assembly 26 to be inserted through a narrow aperture, such as the lumen of suture securement apparatus 10. The pointed tip 28 and/or angular portions 27 allow for one or more sutures to be threaded through the opening provided by insertion assembly 26 and then drawn backward through the narrow aperture. In the illustrated embodiment, the insertion assembly 26 also includes rear angular portions 29 at the rear portion of the insertion assembly 26, proximal to extension tube 14 when insertion assembly 26 is fully inserted through the lumen of suture securement apparatus 10. The angular portions 27, 29 of the insertion assembly 26 are formed by pre-shaped bends in the wire 24 of the insertion assembly 26. The configuration of the pre-shaped bends in insertion assembly 26 allow for bending or pushing together of the opposing sides of the insertion assembly 26 as the insertion assembly 26 is drawn or pushed through narrow apertures. As a result, insertion assembly 26 can be easily threaded through a narrow aperture, such as the lumen of suture securement apparatus 10, and the insertion assembly 26 can readily be retracted back through the aperture. According to one aspect of the present invention a monofilament, braided or other suture or string is provided instead of a wire. Accordingly, the suture will be preloaded into the suture securement apparatus 10 and may be configured to be actuated a single time before disposal of insertion assembly.

In the embodiment of FIG. 1, a suture 32 is utilized in connection with a percutaneous catheter insertion site 30. A percutaneous introducer sheath 60 is inserted at the insertion site 30. FIG. 1A is a close-up view of insertion site 30 showing a dilator tube 62 of percutaneous introducer sheath 60 inserted therein. Suture 32 is configured as a purse string suture. As a result, a plurality of purse string segments 34a, b, c are depicted being positioned around the perimeter of insertion site 30. A first tail 36 is shown extending away from insertion site 30. A second tail 38 is also depicted as extending away from insertion site 30. First tail 36 and second tail 38 are positioned adjacent to one another but in sufficient spatial relationship so as to allow the drawing of first tail 36 closer to second tail 38 to achieve a desired degree of tension on purse string segments 34a, b, c.

In the illustrated embodiment, a user can utilize suture securement apparatus 10 to achieve a desired degree of tension on the purse string configuration of suture 32. To utilize suture securement apparatus 10, a user simply threads the first tail 36 and second tail 38 through opening 25 of insertion assembly 26 formed by wire 24. Once the first tail 36 and second tail 38 are threaded through opening 25 of insertion assembly 26, the user grasps clasp 22 of threading assembly 20 and begins to draw first tail 36 and second tail 38 into extension tube 14. In this manner, complicated or cumbersome introduction of the tips of first tail 36 and second tail 38 into the relatively small diameter of the lumen of extension tube 14 is eliminated. As will be appreciated by those skilled in the art, a variety of suture configurations can be utilized in connection with a variety of types and configurations of puncture wounds and insertion sites. The round or substantially circular wound of percutaneous catheter insertion site 30 as depicted is merely one example.

With continued reference to FIG. 1, introducer sheath 60 includes dilator tube 62, a hub 64 and suture ring 66. Dilator tube 62 of introducer sheath 60 is configured to be percutaneously inserted into the vasculature of a patient, or otherwise positioned within a patient's body. In some situations a practitioner may desire to secure the introducer sheath 60 relative to the patient to minimize the inadvertent movement or accidental full or partial removal of the introducer sheath 60 from its placement within the patient. For example, a introducer sheath 60 may be inserted into the patient with the intention to leave it in place for a significant period of time for repeated use during subsequent procedures.

Suture ring 66 is provided adjacent hub 64 to enable the desired securement of the introducer sheath 60 relative to the body of the patient. Suture ring 66 includes a suture ring aperture 68. Traditionally, suture ring 66 is sutured or tied directly to the body of the patient to secure introducer sheath 60 relative to the patient's body. In the illustrated embodiment, a suture 32 having a first tail 36 and a second tail 38 are threaded into the skin or otherwise secured to the body of the patient. Suture securement apparatus 10 allows for the quick and efficient securement of the suture ring 66 and introducer sheath 60 to the patient, as depicted in FIG. 2 and describe in greater detail below with reference to the same.

As will be appreciated by those skilled in the art, a variety of configurations of threading assembly 20 can be utilized in connection with the suture securement apparatus 10 without departing from the scope and spirit of the present invention. According to one aspect of the present invention, the threading assembly utilizes a hook configuration rather than an insertion assembly 26. According to another embodiment of the present invention, the insertion assembly 26 includes only one or two preformed bends rather than a plurality of preformed bends. According to another embodiment of the present invention, the threading assembly 20 is operable from the distal portion of the suture securement apparatus 10 rather than from the proximal portion of the suture securement apparatus 10.

Figure 2:
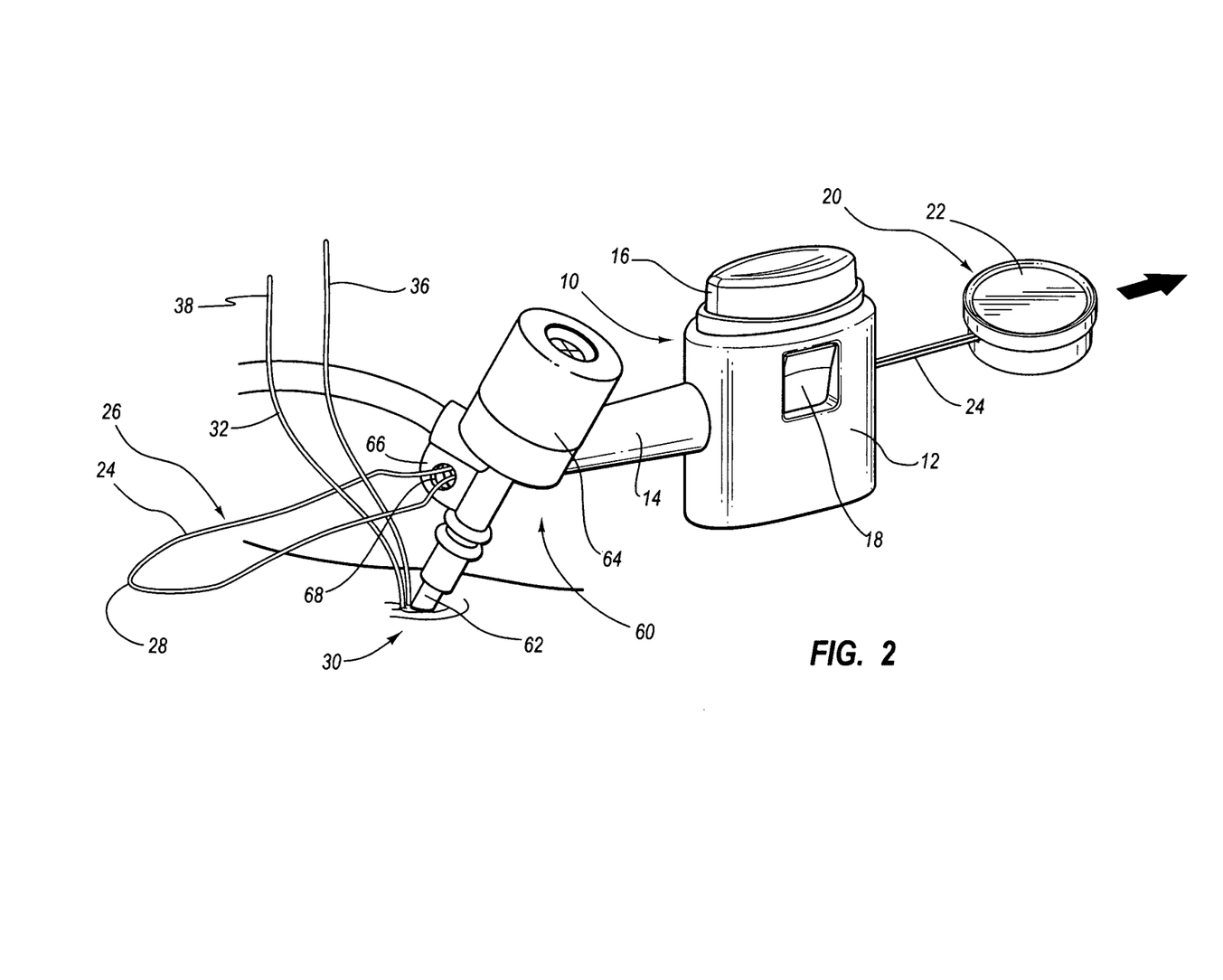
FIG. 2 illustrates the manner in which the threading assembly of the suture securement apparatus is utilized to draw the suture tails through the suture ring of the hub assembly and through the lumen of the suture securement apparatus.

FIG. 2 illustrates utilization of threading assembly 20 to thread first tail 36 and second tail 38 of suture 32 through suture ring aperture 68 and through suture securement apparatus 10. In the illustrated embodiment, insertion assembly 26 is pushed through suture ring aperture 68 of suture ring 66. The first tail 36 and second tail 38 are then threaded through insertion assembly 26. The shape of insertion assembly 26 facilitates the passage or threading of first tail 36 and second tail 38 through insertion assembly 26 in a relatively straight forward and advantageous manner.

Once first tail 36 and second tail 38 have been threaded through insertion assembly 26, the practitioner can retract threading assembly 20 from suture securement apparatus 10. As the user begins to retract threading assembly 20 from suture securement apparatus 10, insertion assembly 26 is pulled through suture ring aperture 68. As insertion assembly 26 is pulled back through suture ring aperture 68, the preformed bends undergo deformation and the sides of insertion assembly 26 are biased together urging the two different sides of insertion assembly 26 together. This allows for insertion assembly 26 to easily be withdrawn through suture ring aperture 68.

As insertion assembly 26 is withdrawn through suture ring aperture 68, first tail 36 and second tail 38 are also pulled through suture ring aperture 68. In this manner, the practitioner does not have to engage in the sometimes tedious and often inconvenient process of threading the tips of first tail 36 and second tail 38 through suture ring 66. As the user continues to withdraw threading assembly 20 from suture securement apparatus 10, insertion assembly 26 is drawn into extension tube 14, along the length of suture securement apparatus 10, and out through the proximal aperture (not shown) of suture securement apparatus 10. In this manner, threading assembly 20 facilitates not only the drawing of first tail 36 and second tail 38 through suture ring 66, but also facilitates the drawing of first tail 36 and second tail 38 through suture securement apparatus 10.

Figure 3:
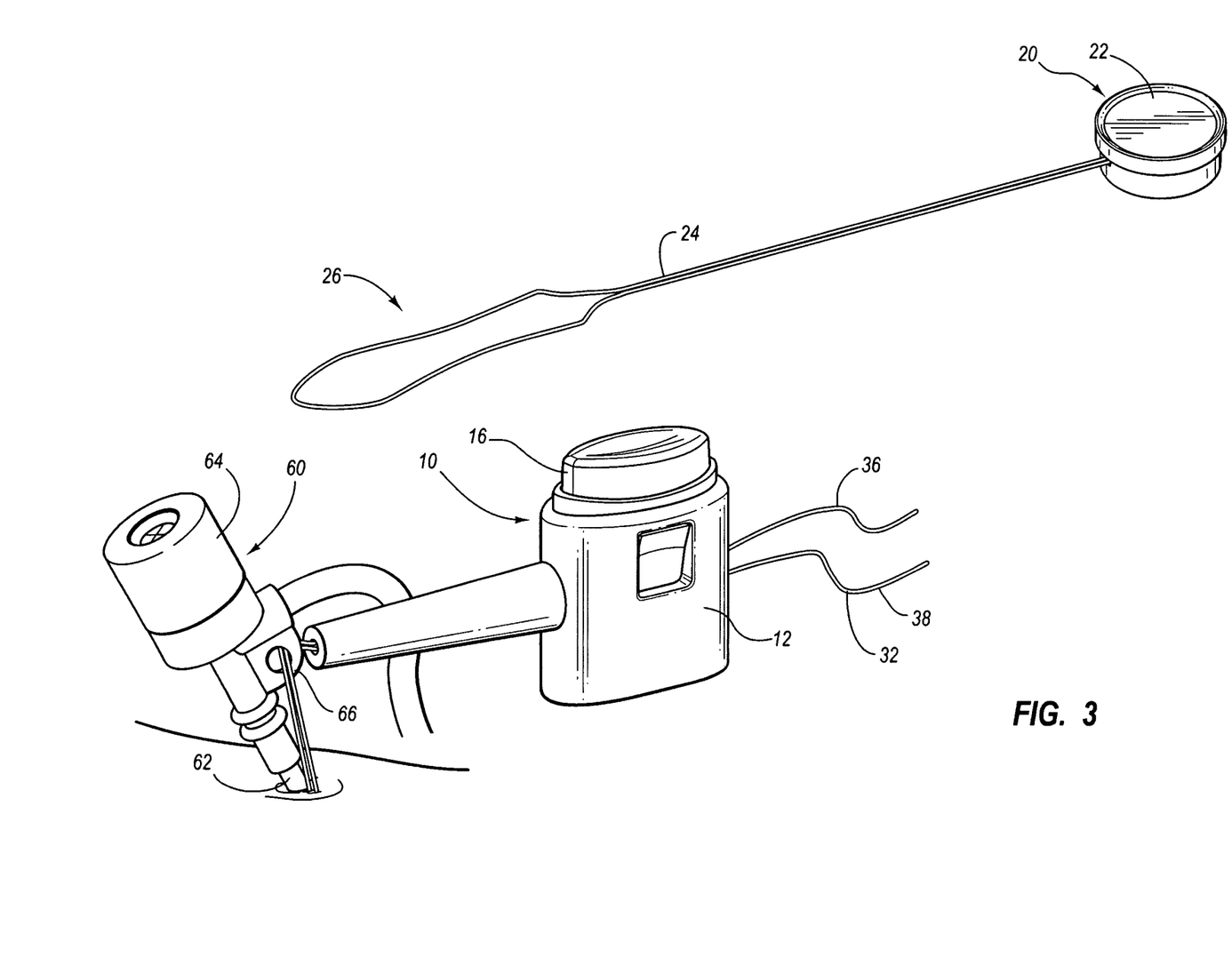
FIG. 3 illustrates the suture securement apparatus operating to secure the suture, and thereby secure the suture ring to maintain the position of the catheter hub relative to the patient.

FIG. 3 illustrates suture securement apparatus 10 after first tail 36 and second tail 38 have been threaded along the length of suture securement apparatus 10. FIG. 3 also illustrates threading assembly 20 once it has been fully withdrawn from suture securement apparatus 10. In the illustrated embodiment, once first tail 36 and second tail 38 have been fully drawn through suture securement apparatus 10, the practitioner can grasp the free ends of first tail 36 and second tail 38 and exert tension on suture 32. To exert tension on suture 32, the practitioner simply depresses release buttons 16 while firmly grasping first tail 36 and second tail 38 and then urges suture securement apparatus 10 in the direction of suture ring 66 of introducer sheath hub 64. By utilizing an adjustable suture securement apparatus 10, the practitioner can increase or decrease the amount of tension of suture 32 and thus the amount of tension holding suture ring 66 relative to the body of the patient. In this manner, introducer sheath 60 is secured relative to the patient and dilator tube 62 is secured in position within the patient.

Figure 4:
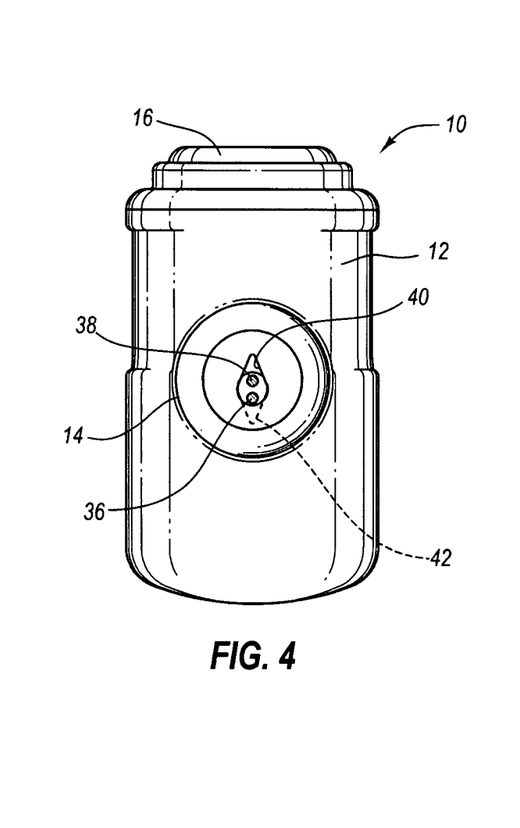
FIG. 4 is an end perspective view of the suture securement apparatus according to one embodiment of the present invention.
Figure 5:
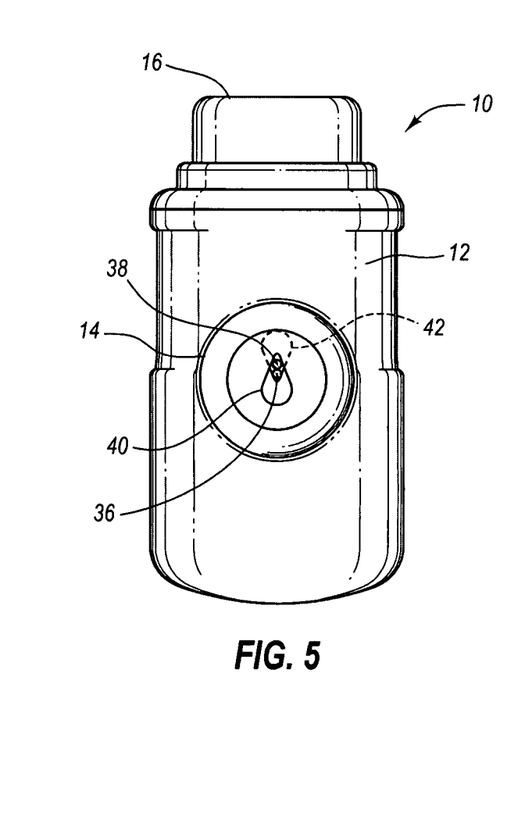
FIG. 5 is an end perspective view of the suture securement apparatus of FIG. 4 illustrating the manner by which the suture securement apparatus engages the tails of the suture positioned within a lumen of the suture securement apparatus according to one embodiment of the present invention.

FIGS. 4 and 5 illustrate an end view of suture securement apparatus 10 according to one aspect of the present invention. In the illustrated embodiment, extension tube 14 is positioned such that a user can look down the extension tube lumen 40. At least a portion of extension tube lumen 40 has a tear drop configuration having a larger or bulbous portion and a smaller width or pointed portion. Additionally, at least a portion of release button lumen 42 has a tear drop configuration, similarly having a bulbous portion and a pointed portion. When release button 16 is fully depressed as depicted in FIG. 4, the bulbous portions of the tear drops are aligned providing a desired larger circumference for accommodating first tail 36 and second tail 38 or also allowing for desired movement of first tail 36 and second tail 38 relative to suture securement apparatus 10.

As the user begins to release the pressure on release button 16, release button 16 moves upward relative to body 12 of suture securement apparatus 10. As a result, the release button lumen 42 begins to change its orientation relative to extension tube lumen 40. As a result, the larger or bulbous portion of the tear drop shape of the extension tube lumen 40 and release button lumen 42 move out of alignment and the pointed portion of the tear drops of extension tube lumen 40 and release button lumen 42 move into alignment as depicted in FIG. 5. This causes cooperative engagement of one or both of first tail 36 and second tail 38 between the pointed portions of the tear dropped configuration of extension tube lumen 40 and release button lumen 42.

The cooperative engagement of first tail 36 and second tail 38 relative to extension tube lumen 40 and release button lumen 42 provides a secure and desired gripping function which allows the practitioner to provide varying degrees of tensioning on first tail 36 and second tail 38. As will be appreciated by those skilled in the art, a variety of types and configurations of lumen cross sections can be provided in connection with extension tube lumen 40 and release button lumen 42 without departing from the scope and spirit of the present invention. For example, according to one embodiment of the present invention, extension tube lumen 40 and release button lumen 42 have a circular, triangular, curvilinear or elliptical shape. According to another embodiment of the present invention, the cross section of all or a portion of extension tube lumen 40 and release button lumen 42 are different from one another.

When a user desires to reposition or fully release first tail 36 and second tail 38, the user simply depresses release button 16 as depicted in FIG. 4. The user then can move suture securement apparatus 10 relative to first tail 36 and second tail 38. For example, the user can depress release button 16 and fully withdraw first tail 36 and second tail 38, for example, by pulling the suture securement apparatus 10 in a rearward direction until first tail 36 and second tail 38 are fully withdrawn from release button lumen 42 and extension tube lumen 40. Alternatively, the user can push release button 16 and draw the free ends of first tail 36 and second tail 38 in a rearward direction to increase the tension exerted on first tail 36 and second tail 38.

Figure 6:
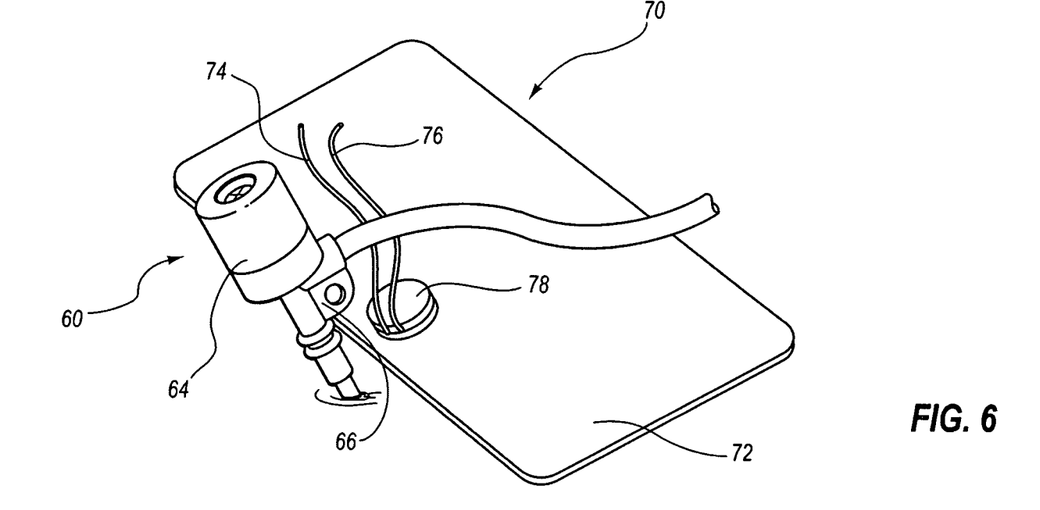
FIG. 6 is an adhesive suture securement device for providing securing sutures which can be utilized to secure a suture ring of a catheter hub without requiring insertion of the sutures through the patient's skin.

FIG. 6 is a perspective view of an adhesive suture securement device 70 according to one embodiment of the present invention. In the illustrated embodiment, adhesive suture securement device 70 comprises an adhesive base 72, a first suture 74, a second suture 76, and an anchor 78. Adhesive suture securement device 70 is utilized to secure sutures 74, 76 relative to a patient's body without requiring puncturing of the patient's skin to secure the sutures 74, 76 relative to the patient. By utilizing adhesive suture securement device 70, the practitioner can quickly and efficiently secure sutures 74, 76 on a patient's skin which can then be utilized for other aspects of the procedure to be performed.

In the illustrated embodiment, adhesive suture securement device 70 is being utilized in connection with a introducer sheath 60. Once the adhesive suture securement device 70 is secured on the skin of the patient, the sutures can then be readily secured to a suture ring 66 of hub 64 of introducer sheath 60. This can effectively secure introducer sheath 60 in a desired placement position relative to the patient. As will be appreciated by those skilled in the art, a single suture or a plurality of sutures comprising more than two sutures can be provided in connection with adhesive suture securement device 70.

In the illustrated embodiment, adhesive base 72 comprises a flexible or inflexible adhesive layer or pad which can be affixed directly to the skin of the patient by utilizing adhesive base 72. Adhesive suture securement device 70 can quickly and easily be placed in a desired position on the patient's skin without requiring a needle prick or other suturing into the patient's skin. By providing a sharpless suture securement solution, patients whose skin tissue is thin or may otherwise be easily damaged, or that may have a fear of needles, can have a suture readily positioned on their skin. Additionally, a sharpless suture securement device provides a mechanism to provide sutures at a percutaneous access site without the drawbacks of a skin puncture that may require healing or that may cause unnecessary concern or fear in the patient.

In the illustrated embodiment, first suture 74 and second suture 76 are secured to adhesive base 72 utilizing an anchor 78. Anchor 78 provides a secure anchoring of first suture 74 and second suture 76 relative to adhesive base 72. In this manner, any pulling or excessive tension exerted on first suture 74 and/or second suture 76 will not result in tearing or the accidental separation of one or more of first suture 74 and second suture 76 from adhesive base 72. In the illustrated embodiment anchor 78 comprises a clam shell type configuration which securely engages one or both first suture 74 and second suture 76 when opposing clam shell type faces of anchor 78 are snapped together. According to one embodiment of the present invention, first suture 74 and second suture 76 do not comprise first and second sutures but rather are opposing end of a continuous suture thread which is secured in the middle of the thread with the opposing tail ends being free such that they can be secured to a suture ring 66 of the introducer sheath 60.

As will be appreciated by those skilled in the art, a variety of types and configurations of anchors can be utilized with adhesive suture securement device 70 without departing from the scope and spirit of the present invention. According to one embodiment of the present invention, anchor 78 has a surface contact area with adhesive base 72 that is greater than four times the total contact area provided between the suture 70 and the adhesive base 72. According to another embodiment of the present invention, anchor 78 secures adhesive base 72 and at least a first suture 74 by sandwiching both adhesive base 72 and the first suture 74 between opposing faces of the anchor 78. According to an alternative embodiment of the present invention, the anchor 78 is positioned only on either the upper face surface or the under surface of the adhesive base 72.

Figure 7:
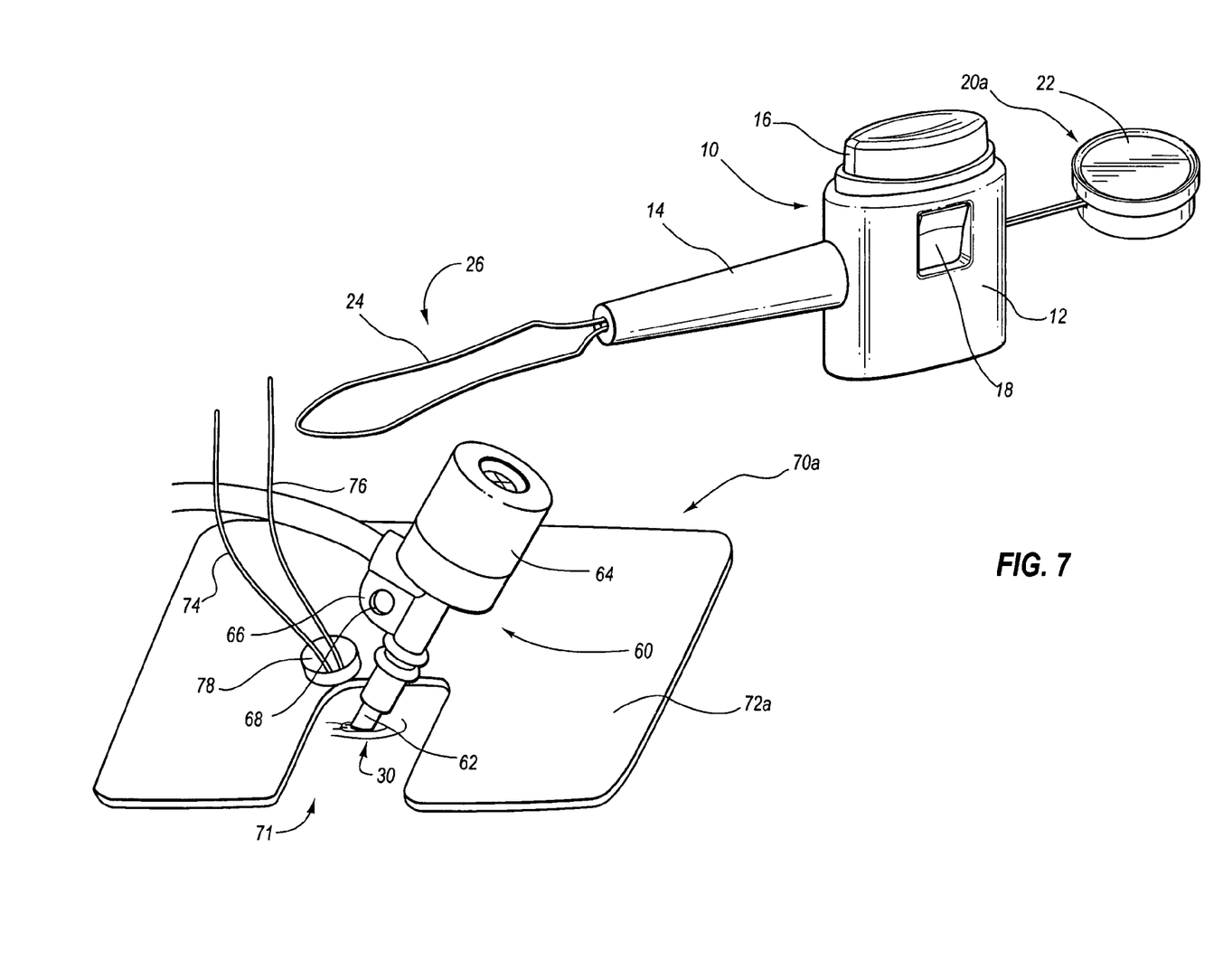
FIG. 7 is an adhesive suture securement device according to an alternative embodiment of the present invention.

FIG. 7 is a perspective view of an adhesive suture securement device 70a according to another embodiment of the present invention. In the illustrated embodiment, adhesive base 72a of adhesive suture securement device 70a has a void 71 which accommodates an apparatus or other securement target while allowing the adhesive base 72a to be positioned around the insertion site 30 of the apparatus or securement target. In other words, void 71 permits adhesive base 72a to be positioned laterally adjacent on two or more lateral sides of dilator tube 62. In the illustrated embodiment, the adhesive suture securement device 70a is utilized in connection with a introducer sheath 60. Additionally in the illustrated embodiment, the adhesive base 72a is formed in a horseshoe-type or semi-circular configuration to define void 71. Anchor 78, first suture 74, and second suture 76 are positioned adjacent void 71 such that any tension on one or both of first suture 74 and second suture 76 are related to a desired position on adhesive base 72a. In the illustrated embodiment, anchor 78, first suture 74 and second suture 76 are positioned approximately at the center or a mid-point of adhesive base 72a such that lateral or other movement of introducer sheath 60 is well secured by adhesive base 72a and other components of adhesive suture securement apparatus 70a.

In the illustrated embodiment, a suture securement apparatus 10 is depicted. Suture securement apparatus 10 is similar to the suture securement apparatus 10 depicted in FIGS. 1, 2 and 3. Suture securement apparatus 10 enables a practitioner to quickly thread first suture 74 and second suture 76 through the suture ring aperture 68 or suture ring 66 of introducer sheath 60 and then to releaseably and adjustably secure the first suture 74 and second suture 76 relative to a medical apparatus, instrument, or other securement target.

As will be appreciated by those skilled in the art, adhesive suture securement device 70a can have a variety of shapes, configurations, uses and other modifications which will enable desired anchoring of the suture relative to a patient. For example, according to one embodiment of the present invention, a central hole is provided as an operative void rather than a partial semi-circular void 71 depicted in FIG. 7. This circular void or hole in the middle of the adhesive base can then be utilized to secure the sutures relative to the patient allowing for the insertion or securement of a medical apparatus position through the patient's skin at an insertion site within the particular void. According to another embodiment a contour, curve or other pad design is provided to allow for desired positioning of the pad relative to a catheter but or other apparatus to be secured.

Figure 8:
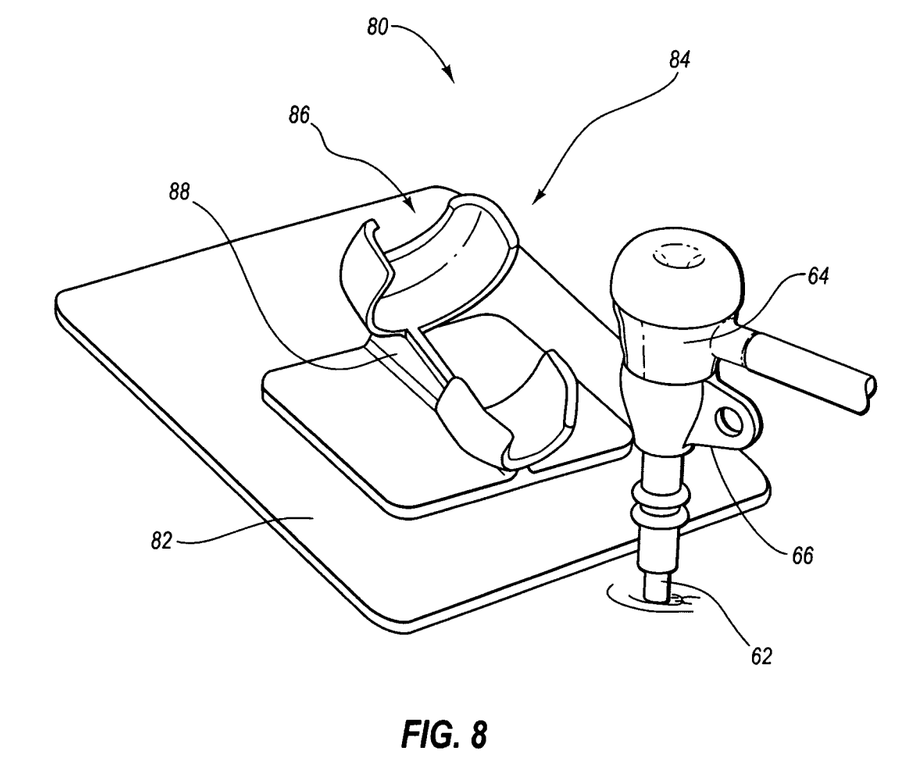
FIG. 8 is a perspective view of an adhesive securement device having a basket securement member for securing a catheter hub relative to a patient without requiring insertion of a suture into a patient's skin according to another embodiment of the present invention.

FIG. 8 is a perspective view of an adhesive securement device 80 having a basket securement member 84 for securing a medical instrument, according to one embodiment of the present invention. Basket securement member 84 comprises a cradle 86, which is secured to an adhesive base 82 utilizing a base 88. Adhesive base 82 is utilized to secure basket securement member 84 relative to a patient. The advantage of utilizing adhesive base 82 is similar to that described with reference to the adhesive base 72 of adhesive suture securement device 70, of FIG. 6, and base 72a of adhesive suture securement device 7a, of FIG. 7. More specifically, a practitioner can secure basket securement member 84 relative to a patient without puncturing the patient's skin.

Cradle 86 of basket securement member 84 is secured to adhesive base 82 utilizing a base 88. Cradle 86 is configured to receive the medical instrument or other securement target while base 88 is utilized to secure cradle 86 relative to adhesive base 82. Cradle 86 is configured to secure and maintain the position of a medical instrument relative to the patient on which adhesive securement device 80 is secured. For example, in the illustrated embodiment, a introducer sheath hub 64 can be positioned within cradle 86 of basket securement member 84. Cradle 86 of basket securement member 84 is shaped to conform to the dimensions and relief surface of hub 64 such that when a user snaps or urges hub 64 into cradle 86, inadvertent movement of hub 64 relative to the patient and relative to the components of adhesive securement device 80 is minimized. According to one embodiment of the present invention, cradle 86 also minimizes rotational movement of hub 64 such that the position of a suture ring 66 relative to cradle 86 is maintained. As will be appreciated by those skilled in the art, the shape of cradle 86 can be modified to the type of medical apparatus or securement target with which basket securement member 84 is to be utilized.

As will be appreciated by those skilled in the art, a variety of types and configurations of basket securement members 84 can be utilized without departing from the scope and spirit of the present invention. For example, according to one embodiment of the present invention, the basket securement member 84 includes a top clam shell or lid portion which facilitates securement of the securement target relative to the other components of adhesive securement device 80. According to another embodiment of the present invention, an adhesive overlay is provided which secures the components of adhesive securement device 80.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture securement apparatus for selectively and releasably securing a suture ring of a catheter in connection with sutures positioned adjacent the suture ring of the catheter, the suture securement apparatus comprising:
    a body having a cavity positioned therein;
    a plunger slidably disposed within the cavity of the body and biased to secure the sutures and enable releasable engagement of the sutures;
    an extension tube extending a predetermined distance from the body such that a tip of the extension tube is adaptable to engage the sutures adjacent to an insertion point of the sutures without interference from the body; and
    a threading assembly having a base and a suture engaging portion to facilitate threading of the sutures through the suture ring and through a lumen of the suture securement apparatus,
    wherein the plunger comprises a plunger lumen through the plunger, wherein the plunger lumen forms a portion of the lumen of the suture securement apparatus,
    wherein the plunger lumen is configured to have a cross-section in the shape of a tear drop, and wherein at least a portion of a lumen of the extension tube is configured to have a cross-section in the shape of a tear drop and oriented such that a pointed portion of the tear drop is oriented 180 degrees relative to the pointed portion of the tear drop shape of the plunger lumen cross-section and wherein the plunger is slidably disposed within the body such that the cross-section of the plunger lumen is configured to move substantially along a plane parallel to the cross-section of the extension tube lumen to secure and release the sutures such that when the sutures are secured by the suture securement device the sutures are engaged between pointed portions of the tear drop shapes of the plunger lumen and extension tube and
    wherein when the plunger is in a fully depressed position, rounded portions of the tear drop shaped cross sections of the plunger lumen and the extension tube lumen are aligned such that the sutures are displaceable with respect to the suture securement apparatus when the sutures are also extending through the opening and the extension tube lumen.

2. A suture securement apparatus of claim 1, wherein the plunger comprises a release button.

3. A suture securement apparatus of claim 1, wherein the plunger is biased toward an undepressed position.

4. A suture securement apparatus of claim 1, wherein the suture engaging portion of the threading assembly comprises a wire.

5. A suture securement apparatus of claim 4, wherein the wire comprises an insertion assembly having a pointed tip and one or more angular portions to facilitate threading the insertion assembly through the lumen of the suture securement apparatus.

6. A suture securement apparatus of claim 1, wherein the suture engaging portion of the threading assembly comprises a suture, monofilament, or braided string.

7. A suture securement apparatus of claim 1, wherein when the plunger is in a fully depressed position, a portion of the tear drop shape having a larger cross-section and being associated with the plunger is aligned with a portion of the tear drop shape having a larger cross-section and being associated with the extension tube such that a suture threaded through the lumen of the suture securement apparatus is released and moveable relative to the suture securement apparatus, and wherein when the plunger is in a fully undepressed position the pointed portion of the tear drop shape cross-section of the plunger is aligned with a pointed portion of the tear drop shaped cross-section of the extension tube such that a suture threaded through the lumen of the suture securement apparatus is engaged and secured relative to the suture securement apparatus.

8. A suture securement apparatus of claim 1, wherein when the suture is secured by the suture securement device, top and bottom portions of the suture as well as lateral portions of the suture are engaged by portions of the tear drop shapes of the plunger lumen and the extension tube lumen.

9. A suture securement assembly, comprising:
    a suture securement apparatus comprising:
        a body; and
        a plunger slidably disposed with respect to the body, the plunger comprising an opening configured to accommodate a portion of a suture, the opening comprising a first tear drop shaped cross-section;
        an extension tube extending from the body, the extension tube defining an extension tube lumen, a portion of the extension tube lumen comprising a second tear drop shaped cross-section, wherein the first and second tear drop shaped cross-sections are oriented such that pointed portions of each tear drop extend in opposite directions and wherein slidable displacement of the plunger with respect to the body displaces the first and second cross-sections in parallel planes; and
    a threading assembly comprising a base and a suture engaging portion to facilitate threading of a portion of the suture through a suture ring and through the suture securement apparatus;
    wherein the plunger is biased such that in a released configuration the suture extending through the opening and the extension tube lumen tends to be engaged between the pointed portions of each tear drop shaped cross-section and
    wherein when the plunger is in a fully depressed position, rounded portions of each tear drop shaped cross section are aligned such that the suture extending through the opening and the extension tube lumen is displaceable with respect to the suture securement apparatus.

10. The suture securement assembly of claim 9, wherein the plunger comprises a release button.

11. The suture securement assembly of claim 9, wherein the plunger is biased toward an undepressed position.

12. The suture securement assembly of claim 9, wherein the suture engaging portion of the threading assembly comprises a wire.

13. The suture securement assembly of claim 9, wherein the suture engaging portion of the threading assembly comprises a suture, monofilament, or braided string.

14. The suture securement assembly of claim 12, wherein the wire comprises an insertion assembly having a pointed tip and one or more angular portions to facilitate threading the insertion assembly through the lumen of the suture securement apparatus.

15. The suture securement assembly of claim 9, wherein the pointed portions of each tear drop shaped cross-section engage the suture extending through the opening and the extension tube lumen on top, bottom, and lateral portions of the suture.

16. The suture securement device of claim 9, wherein the plunger is biased such that in the released configuration forces between the plunger and the body tend to push the suture extending through the opening and the extension tube lumen toward the pointed portions of each tear drop shape cross-section.

17. A suture securement device, comprising:
 a body; and
 a plunger slidably disposed with respect to the body, the plunger comprising an opening configured to accommodate a portion of a suture, the opening comprising a first tear drop shaped cross-section;
 a lumen extending through the body, a portion of the lumen comprising a second tear drop shaped cross-section, wherein the first and second tear drop shaped cross-sections are oriented such that pointed portions of each tear drop extend in opposite directions and wherein slidable displacement of the plunger with respect to the body displaces the first and second cross-sections in parallel planes; and
 wherein the plunger is biased such that in a released configuration the suture tends to be engaged between the pointed portions of each tear drop shaped cross-section when the suture is also extending through the opening and the lumen, and
 wherein when the plunger is in a fully depressed position, rounded portions of each tear drop shaped cross section are aligned such that the suture is displaceable with respect to the suture securement apparatus when the suture is also extending through the opening and the lumen.

18. The suture securement device of claim 17, wherein the plunger is biased such that in the released configuration forces between the plunger and the body tend to push the suture toward the pointed portions of each tear drop shape cross-section when the suture is also extending through the opening and the lumen.

19. The suture securement device of claim 17, wherein the plunger comprises a release button.

20. The suture securement device of claim 17, wherein the plunger is biased toward an undepressed position.

21. The suture securement device of claim 17, wherein the pointed portions of each tear drop shaped cross-section engage the suture on top, bottom, and lateral portions of the suture when the suture is also extending through the opening and the lumen.

* * * * *